United States Patent [19]

McCoy

[11] Patent Number: 5,055,101
[45] Date of Patent: * Oct. 8, 1991

[54] VARIABLE SHAPE GUIDE APPARATUS

[75] Inventor: William C. McCoy, Zionsville, Ind.

[73] Assignee: Catheter Research, Inc., Indianapolis, Ind.

[*] Notice: The portion of the term of this patent subsequent to Jul. 19, 2005 has been disclaimed.

[21] Appl. No.: 447,927

[22] Filed: Dec. 8, 1989

Related U.S. Application Data

[63] Continuation of Ser. No. 103,926, Oct. 2, 1987, Pat. No. 4,944,727, which is a continuation-in-part of Ser. No. 870,926, Jun. 5, 1986, Pat. No. 4,758,222, which is a continuation-in-part of Ser. No. 728,634, May 3, 1985, Pat. No. 4,601,705, which is a continuation-in-part of Ser. No. 547,402, Oct. 31, 1983, Pat. No. 4,543,090.

[51] Int. Cl.$^5$ ............................................. A61M 37/00
[52] U.S. Cl. ....................................... 604/95; 604/281; 128/657; 128/772
[58] Field of Search ................. 604/95, 264, 280, 281; 128/4, 6, 657, 772; 606/78

[56] References Cited

U.S. PATENT DOCUMENTS

| | | | |
|---|---|---|---|
| 3,043,309 | 7/1962 | McCarthy | 128/348 |
| 3,521,620 | 7/1970 | Cook . | |
| 3,547,103 | 12/1970 | Cook . | |
| 3,605,725 | 9/1971 | Bentov | 128/2.05 R |
| 3,674,014 | 7/1972 | Tillander | 128/2.05 R |
| 3,729,008 | 4/1973 | Berkovits | 128/418 |
| 3,773,034 | 11/1973 | Burns et al. | 128/2 M |
| 3,868,956 | 3/1975 | Alfidi et al. | 606/78 |
| 3,890,977 | 6/1975 | Wilson | 128/418 |
| 4,146,019 | 3/1979 | Bass et al. | 128/6 |
| 4,176,662 | 12/1979 | Frazer | 128/6 |
| 4,427,000 | 1/1984 | Ueda | 128/6 |
| 4,456,017 | 6/1984 | Miles | 128/772 |
| 4,543,090 | 9/1985 | McCoy | 604/95 |
| 4,582,181 | 4/1986 | Samson . | |
| 4,586,923 | 5/1986 | Gould et al. | 604/95 |
| 4,601,283 | 7/1986 | Chikama | 128/4 |
| 4,601,705 | 7/1986 | McCoy | 604/95 |
| 4,616,656 | 10/1986 | Nicholson et al. | 128/630 |
| 4,641,654 | 2/1987 | Samson et al. . | |
| 4,742,817 | 5/1988 | Kawashima et al. | 128/4 |
| 4,748,986 | 6/1988 | Morrison et al. | 128/772 |
| 4,753,223 | 6/1988 | Bremer | 128/4 |
| 4,758,222 | 7/1988 | McCoy | 604/95 |
| 4,776,844 | 10/1988 | Ueda | 604/281 |
| 4,790,624 | 12/1988 | Van Hoye et al. | 350/96.26 |
| 4,799,474 | 1/1989 | Ueda | 604/281 |
| 4,838,859 | 6/1989 | Strassmann | 604/95 |
| 4,884,557 | 12/1989 | Takehana et al. | 128/4 |
| 4,934,340 | 6/1990 | Ebling et al. | 604/95 |
| 4,944,727 | 7/1990 | McCoy | 604/95 |

Primary Examiner—Stephen C. Pellegrino
Assistant Examiner—Ralph A. Lewis
Attorney, Agent, or Firm—Barnes & Thornburg

[57] ABSTRACT

A maneuverable distal apparatus includes a temperature-activated memory element moving in a first direction to assume a predetermined shape when heated to a predetermined temperature and control means for selectively heating the memory element so that the memory element is moved in the first direction. A spring is provided for yieldably urging the memory element in a second direction away from the first direction upon cooling of the memory element to a temperature less than the predetermined temperature so that the memory element is moved to assume a shape other than the predetermined shape.

6 Claims, 5 Drawing Sheets

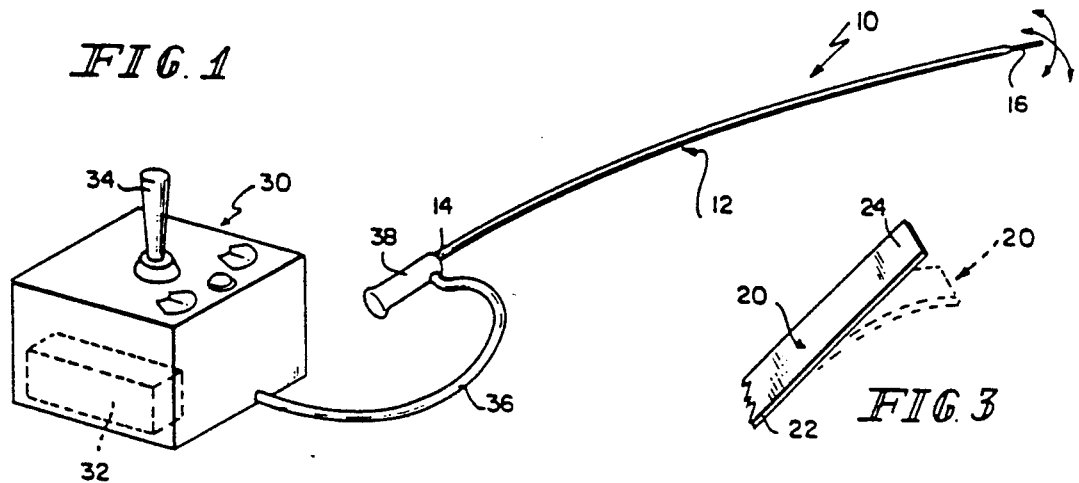
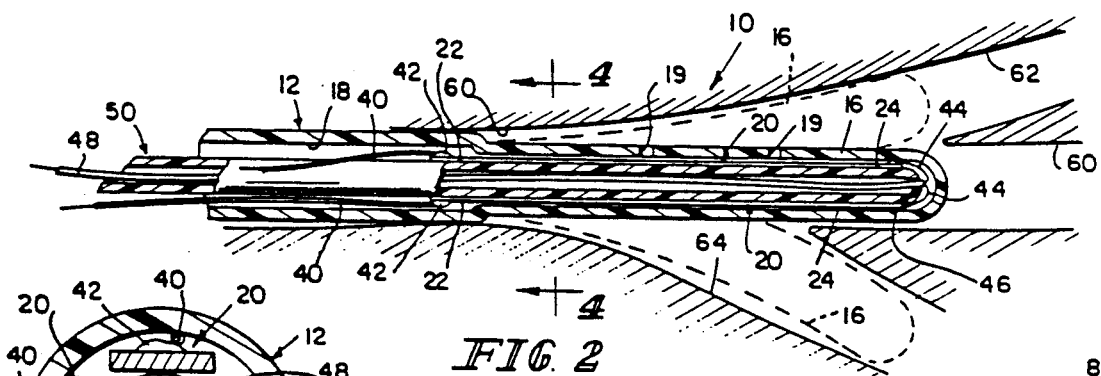
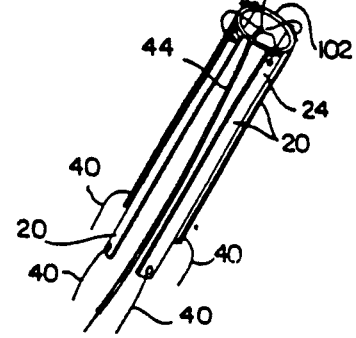
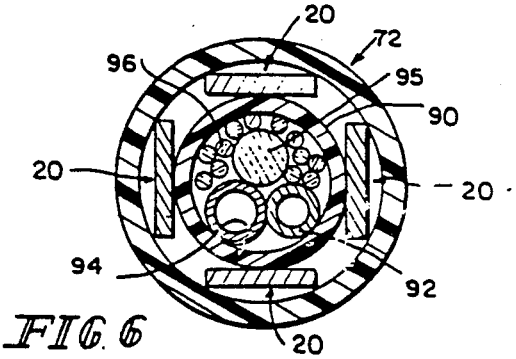

VARIABLE SHAPE GUIDE APPARATUS

This is a continuation of application Ser. No. 103,926 filed Oct. 2, 1987 now U.S. Pat. No. 4,944,727, which is a continuation-in-part of copending application Ser. No. 870,926, filed June 5, 1986 now U.S. Pat. No. 4,758,222, which is a continuation-in-part of copending application Ser. No. 728,634 filed May 3, 1985, now U.S. Pat. No. 4,601,705, which is a continuation-in-part of application Ser. No. 547,402 filed Oct. 31, 1983, now U.S. Pat. No. 4,543,090.

BACKGROUND AND SUMMARY OF THE INVENTION

The present invention relates to guide apparatus, probes, and the like, and particularly to guide apparatus that are steerable through body cavities and aimable at obstructions, organs, or tissue within the body from a position external to the body. More particularly, the present invention relates to maneuverable guide apparatus including spring means for biasing a temperature-activated memory element to alter the shape of the memory element upon cooling of the memory element to a temperature below its martensitic transformation temperature.

Some attempts have been made in the past to provide catheters having distal ends which, when inserted into a body, are manipulatable to advance the catheter through body cavities. See for example, U.S. Pat. Nos. 3,674,014 and 3,773,034. The catheter disclosed in U.S. Pat. No. 3,674,014 includes permanent magnets and employs a magnetic field to bend the distal end of the catheter. The catheter disclosed in U.S. Pat. No. 3,773,034 includes fluid conduits and employs a fluid to bend the distal end of the catheter. Other controlled devices are disclosed in U.S. Pat. Nos. 3,605,725 and 4,176,662. However, these prior devices are quite difficult to control and manipulate.

Some work has previously been done to produce a catheter which is readily insertable while being effectively anchorable in a body cavity. See, for example, U.S. Pat. Nos. 3,729,008 and 3,890,977.

In U.S. Pat. No. 3,890,977 to Wilson, the distal end of the catheter is formed into a desired shape by using a material exhibiting mechanical memory that is triggered by heat. By heating the mechanical memory material, the distal end of the catheter is shaped to anchor the catheter within the body. However, the change of the shape or other movement of the distal end in these prior devices is limited to a single direction. Once the memory material has been heated causing the distal end to move in said single direction to assume its characteristic anchoring shape, it becomes necessary to deform the distal end manually at a temperature below the transition temperature of the mechanical memory material in order to change the shape of the distal end. The need for manual manipulation of a catheter once it is inserted into body limits the steerability and aimability of the catheter.

Other devices are known for guiding a catheter to a particular location within the body. See for example U.S. Pat. No. 3,043,309.

One object of the present invention is to provide a steerable guide apparatus, probe, and the like which is easy to operate and steerable in a plurality of different directions within the body.

Another object of the present invention is to provide an aimable guide apparatus, probe, and the like which is easy to operate and which can be aimed at obstructions, organs, or tissues in a plurality of different directions within the body.

Yet another object of the present invention is to provide a guide apparatus, probe, and the like of improved maneuverability having means for slidably coupling each of a plurality of temperature-activated memory elements to a core member so that each memory element is permitted to slip in relation to the adjacent core member when at least one of the memory elements is heated to assume a predetermined "memorized" shape.

Another object of the present invention is to provide a steerable and aimable guide apparatus, probe, and the like of very simple design having only one temperature-activated memory element that is movable to a predetermined shape using remote controls to steer and aim the guide apparatus and yet is automatically returnable to an initial shape without manual manipulation by an operator.

Still another object of the present invention is to provide a highly maneuverable guide apparatus, probe, and the like having at least one resilient element for biasing the distal end of the guide apparatus to assume an initial shape and a separate temperature-activated memory element that is movable under heat to bend the distal end of the guide apparatus to a multiplicity of shapes other than the initial shape.

Another object of the present invention is to provide a steerable and aimable guide apparatus, probe, and the like of simple construction wherein a memory element is employed to deflect a guide wire made of spring material.

Yet another object of the present invention is to provide a steerable and aimable guide apparatus, probe, and the like wherein the guide wire is made of a resilient shape-memory material.

Still another object of the present invention is to provide a steerable and aimable guide apparatus, probe, and the like wherein a temperature-activated memory element made of a shape-memory alloy and employed to deflect a guide wire made of spring material is coupled to the guide wire to apply an axial compression pulling force to the guide wire as the length of the memory element is shortened upon being heated to a predetermined temperature in accordance with a thermal property of the shape-memory alloy so that the guide wire is "pulled" along its axis by the memory element to assume a different shape.

According to the present invention, a maneuverable distal apparatus includes a temperature-activated memory element moving in a first direction to assume a predetermined shape when heated to a predetermined temperature and spring means for yieldably urging the memory element in a second direction away from the first direction upon cooling of the memory element to a temperature less than the predetermined temperature so that the memory element is moved to assume a shape other than the predetermined shape. The apparatus also includes insulation means for preventing unwanted electrically conductive contact between the memory element and the spring means and control means for selectively heating the memory element so that the memory element is moved in the first direction.

In preferred embodiments, the spring means is an elongated coil spring formed to include a longitudinal cavity and the memory element is positioned in the longitudinal cavity. The insulation means includes a tubular sleeve positioned in the longitudinal cavity and the memory element is positioned in the tubular sleeve. An end cap is coupled to a distal end of the elongated coil spring and the insulation means includes means for preventing electrically conductive contact between the memory element and the end cap.

The control means includes power supply means, first electrical lead means for coupling the power supply means and the spring means in electrical communication, and second electrical lead means for coupling the power supply means and the memory element in electrical communication. Circuit means interconnecting the spring means and the memory element is provided for establishing an electrical circuit electrically connecting the spring means, the memory element, and the control means in series.

In another preferred embodiment, the guide wire is a tubular coiled spring made of a resilient shape-memory alloy. Control means is provided for selectively heating the tubular coiled spring to at least a predetermined temperature so that the tubular coiled spring moves from its initial shape to assume its predetermined shape. The tubular coiled spring returns toward its initial shape upon being cooled to a temperature less than the predetermined temperature.

In yet another embodiment, the memory element is disposed inside a hollow axially compressible guide wire made of spring material and anchored at its opposite ends to spaced-apart distal and proximal portions of the guide wire. The "double-anchored" memory element shortens in length in accordance with due to a characteristic thermal property of the shape-memory alloy comprising the memory element upon being heated to a predetermined temperature. Such shortening acts to apply an axial compression load to the axially compressible guide wire, thereby effectively "pulling" the guide wire to assume a different shape. The guide wire returns toward its initial shape upon cooling of the memory element to a temperature less than the predetermined temperature due, in part, to spring characteristics of the guide wire. One notable advantage of this double-anchored feature is that the size and mass of the memory element can be reduced significantly in comparison to other embodiments since less force is required to pull the guide wire to a different shape than to push the guide wire to the same shape. It will be understood that "pulling" refers generally to axial compression loading or the like of the guide wire, while "pushing" refers generally to transverse shear loading or the like of the guide wire.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 1 is a perspective view of a steerable and aimable guide apparatus embodying the present invention;

FIG. 2 is a longitudinal cross-sectional view, partly broken away, of a body cavity and the distal end of the guide apparatus shown in FIG. 1;

FIG. 3 is a perspective view of an embodiment of a temperature-activated memory element employed in the guide apparatus showing its different shapes;

FIG. 4 is a transverse cross-sectional view of the distal end of the guide apparatus embodying the present invention taken generally along section lines 4—4 in FIG. 2;

FIG. 5 is a longitudinal cross-sectional view of a body cavity showing the aimable feature of a guide apparatus embodying the present invention;

FIG. 6 is a transverse cross-sectional view of the embodiment of the guide apparatus shown in FIG. 5 taken generally along section lines 6—6 of FIG. 5;

FIG. 7 is a perspective view of an embodiment of a plurality of temperature-activated memory elements employed in the distal end of the guide apparatus to deflect or move the distal end for steering and aiming thereof;

DETAILED DESCRIPTION OF THE DRAWINGS

Figure 8:
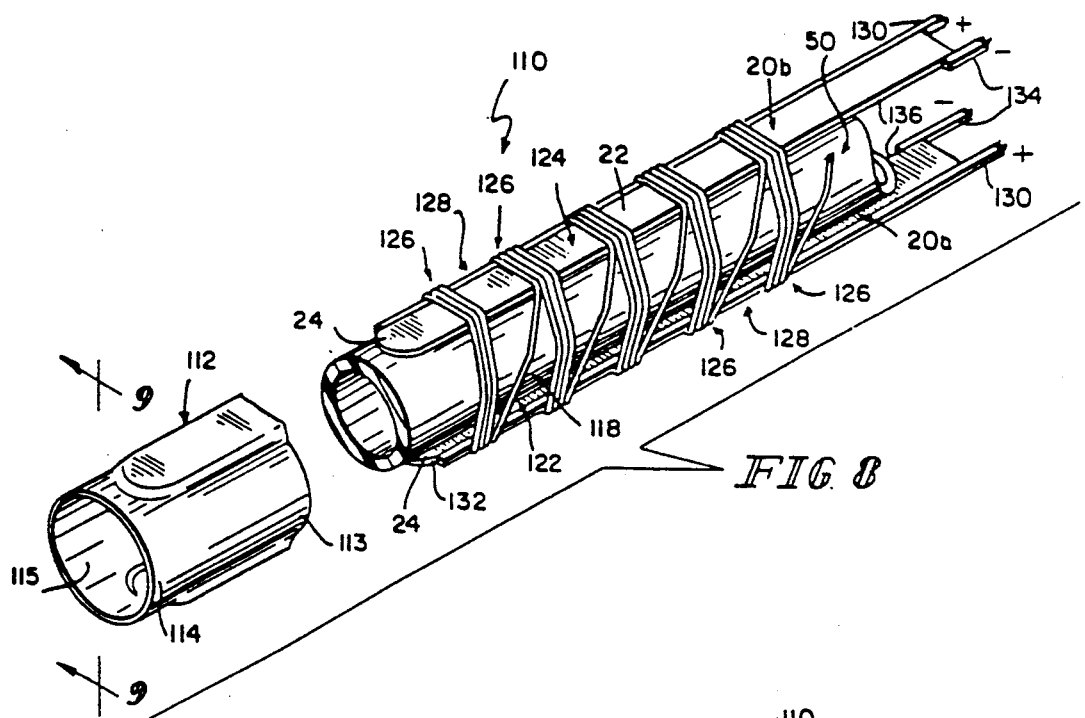
FIG. 8 is an exploded view of another embodiment of the present invention.

A catheter 10 embodying the present invention is shown generally in FIG. 1. Catheter 10 includes an elongated tubular member 12 having a proximal end 14 and a steerable and aimable distal end 16. In the illustrative embodiment, the tubular member 12 is formed of plastic, TEFLON, or cross-linked kynar or polyethylene. As will become apparent in the description of catheter 10, it is desirable that tubular member 12 be formed of a material that is flexible, that can withstand heat, and which provides electrical insulation.

As best shown in FIG. 2, the tubular member 12 can have a lumen 18 for the passage of fluid from the proximal end 14 to the distal end 16 and vice versa. Typically, the tubular member 12 includes one or more holes or openings 19 through which fluids are either injected into or drained from a body cavity. Some cannulae may have an open distal end 16 for insertion and withdrawal of medical instruments.

As shown in FIGS. 2 and 3, a plurality of temperature-activated memory elements 20 are incorporated into the distal end 16 of the tubular member 12. It may be desirable to isolate the memory elements 20 from the body cavity. The temperature-activated memory elements 20 preferably exhibit a memory characteristic in response to temperature changes. The elements 20 may be wires or flat strips such as shown in FIG. 3. In the illustrative embodiment, the temperature-activated memory elements 20 are formed of a mechanical memory metal such as a nickel titanium alloy. While a nickel titanium alloy is desirable, other metal elements having a memory characteristic related to temperature could be used without departing from the scope of the invention. Such metal elements should have a high resistance to electric current so that heat is produced when current is passed therethrough.

As shown in FIG. 3, the elements 20 have a body portion 22 and a tip portion 24. Each element 20 has a first or preset shape represented by the broken lines in FIG. 3 and a second shape represented by the solid lines in FIG. 3. Illustratively, the preset shape is an arcuate shape, and the second shape is a straight shape. It will be appreciated that the preset shape could be any shape.

Each temperature-activated memory element 20 is originally annealed into its preset shape (represented by the broken lines in FIG. 3). Memory elements 20 are cooled and straightened to their second shape (represented by the solid lines in FIG. 3) before incorporation into the distal end 16 of the tubular member 12. When the elements 20 are again heated to a predetermined transitional temperature they return to their preset shape. By applying an opposing force to an element 20 that has moved to assume its preset shape it can be moved to its second shape (represented by the solid lines in FIG. 3). In the illustrative embodiment, the predetermined transitional temperature is any temperature above body temperature. For example, the predetermined transitional temperature may be in the range of 100° to 150° F.

The memory elements 20 can either be directly incorporated into the distal end 16 of the tubular member 12 or can be carried on an electrically insulative core 50. As will be discussed later, each memory element 20 must be coupled to at least one other memory element 20 so that when one of the memory elements is heated it applies a force to move the other memory element 20.

The catheter 10 further includes an electronic control system 30 for controlling current flow to vary the temperature of each temperature-activated memory element 20 from a position external to the body so as to deflect the distal end 16 of the tubular member 12 in a plurality of different directions corresponding to the preset shapes of the elements 20. The control system 30 includes a power supply source 32 which may be either AC or DC. The system 30 also includes a control device 34 which, in the illustrative embodiment, is similar to a "joystick" control, tactile membrane switch, or ball controller. It will be appreciated that various types of control devices 34 may be employed without departing from the scope of the present invention.

The power supply source 32 is coupled through control device 34 to the tubular member 12 by cable 36 and a coupling device 38. Further, the temperature-activated memory elements 20 are electrically connected to the control device 34 through cable 36 and coupling 38 by electrical wires 40 which are attached to the body portions 22 of memory elements 20 by conventional means 42 such as soldering or crimping. Return or ground wires 44 are attached to the tip portions 24 of memory elements 20 by conventional means such as soldering or crimping 46. Return or ground wires 44 may be combined into a single ground cable 48 as shown in FIG. 2.

In the embodiment illustrated in FIG. 2, the temperature-activated memory elements 20 are carried on the exterior of the core 50 and ground wire 48 runs through the interior of the core 50. Core 50 couples each memory element 20 to at least one other memory element 20 so that when a memory element 20 moves to assume its preset shape in response to heat it applies a force to move the other memory element 20 coupled thereto. In preferred embodiments, the core 50 is a tube formed of urethane having a wall thickness of about 0.005 inch. In other embodiments, the core 50 may be a fiber optics bundle, electrical wire, microinstrumentation, or any other suitable member. Other mounting arrangements could be used for incorporating the memory elements 20 into the distal end 16 of the tubular member 12 without departing from the scope of the present invention.

In operation, the distal end 16 of the tubular member 12 is inserted into a body cavity 60 such as a blood vessel while memory elements 20 are straight and at a temperature below the transitional temperature. At this stage, each memory element 20 is in its second shape for ready insertion of the distal end 16 into the body cavity 60. The tubular member 12 is pushed through cavity 60 until it reaches a desired branch 62 or 64 extending from the cavity 60. Control device 34 is manipulated to apply an electrical voltage or current to one or more of the memory elements 20. Because of the high resistance of memory elements 20, heat is generated. When a memory element is heated to its predetermined transitional temperature (i.e., a predetermined temperature above body temperature) the memory element 20 moves to assume its preset shape (as shown by the broken lines in FIG. 3), thereby deflecting or moving the distal end 16 of tubular member 12 into one of the desired branch cavities 62 or 64. Once the distal end 16 is in the branch 62 or 64, power can be removed from the memory element 20 to allow it to cool. While the memory element 20 is at a temperature above its predetermined transitional temperature it remains relatively stiff in its preset shape. When the memory element 20 cools to a temperature below its predetermined transitional temperature it becomes soft or pliable in its preset shape. After cooling, a voltage or current is applied to another memory element 20 coupled to the cooled memory element 20 still in its preset shape. When the other memory element 20 reaches its predetermined transitional temperature, it begins to move to assume its preset shape and in doing so applies a force to the memory element 20 coupled thereto to move it to its second shape (as shown by the solid lines in FIG. 3). The catheter tubular member 12 can continue to be pushed through the branch 62 or 64 until it is again desirable to turn or bend the catheter 10.

As illustrated in FIG. 4, four temperature-activated memory elements 20 may be carried on the exterior of core 50. In the illustrative embodiment, pairs of the memory elements 20 are shown diametrically opposed to each other so that opposed elements 20 apply forces to each other when they are heated. Thus, the distal end 16 may be deflected in at least four different directions by applying an electrical current or voltage to one of the memory elements 20. It will be appreciated that more or less than four memory elements 20 may be utilized without departing from the scope of the present invention. However, it should be noted that at least two memory elements 20 are required. Further, it may be desirable to apply an electrical voltage or current to more than one of the memory elements 20 simultaneously to increase the number of directions in which the distal end 16 of the tubular member 12 may be deflected. The control system 30 may include means for regulating the application of current or voltage applied to the memory elements 20 to allow virtually an unlimited number of directions in which the distal end 16 may be deflected for the purpose of steering the catheter tubular member 10 through body cavities. It will be appreciated that a large number of wire memory elements could be incorporated into the distal end 16 and a voltage or current applied to one or more of the wires to deflect the distal end 16 in a desired direction.

Another application for a catheter 70 embodying the present invention is shown in FIGS. 5 and 6. Reference numerals from FIGS. 1-4 have been applied to the catheter 70 shown in FIGS. 5 and 6 where the same or similar parts are being used. Catheter 70 includes a tubular member 72 having a distal end 76. The distal end 76 includes a plurality of temperature-activated memory elements 20 of the type previously described. The same or similar control system may be employed in connection with the catheter 70 in a body cavity 80 for the purpose of aiming the distal end 76 at an obstruction, organ, or tissue 82 within the cavity 80. The catheter 70 may be anchored in the cavity 80 by a balloon 78. Once the catheter 70 is anchored, the distal end 76 is aimed in one of a plurality of directions to establish a course for the injection of fluid or a laser beam at the organ or tissue 82.

As shown in FIG. 6, a core 90 formed of insulative material passes through tubular member 72. Memory elements 20 are carried on the core 90 between the core 90 and the tubular member 72. Core 90 serves to couple each memory element 20 to at least one other memory element 20 in the manner and for the purpose previously described. The hollow core 90 may include a first tube 92 for carrying a fluid from the proximal end of the catheter 70 to the distal end 76. A return tube 94 may be included for extracting fluid. It will be appreciated that either passage 92 or 94 may be used for inserting a medical instrument into the cavity 80. Core 90 may also include a transparent member 95 providing a lens for observing the obstruction, organ, or tissue 82 and a bundle of fiber-optic lines 96 for transmitting light or a laser beam to the distal end 76. Thus, in the embodiment illustrated in FIGS. 5 and 6, catheter 70 has a distal end 76 which is aimable in a plurality of directions in accordance with the present invention for the purpose of establishing a course for the injection of fluid, light, or a laser beam at an obstruction, organ, or tissue 82.

Another embodiment of an arrangement for the memory elements 20 is shown in FIG. 7. The memory element arrangement 100 includes a plurality of memory elements 20 coupled at their distal ends 24 by a thermally and electrically insulative ring 102. Various materials, such as plastic, may be used to construct the ring 102. Ground wires from each memory element 20 are channeled through a common ground wire conduit 44. Ring 102 serves to couple the memory elements 20 to each other and performs a function similar to cores 50 and 90. This arrangement facilitates the mounting of the memory elements 20 in the distal end 16, 76 of the catheters 10, 70, respectively.

Yet another embodiment of the present invention is shown in FIGS. 8-11. Reference numerals from FIGS. 1-4 have been applied to a catheter 110 shown in FIGS. 8-11 where the same or similar parts are being used. Catheter 110 includes a tubular member 12, a pair of temperature-activated memory elements 20a and 20b, and a core 50 of the types described above. Memory elements 20a and 20b may be flat as shown in FIGS. 8-11 or in some applications may be wires, particularly where more than two memory elements are employed. The catheter 110 further includes a sleeve 112 for slidably coupling each memory element 20a,b to the core member 50 so that each memory element 20a,b is permitted to slip in relation to the adjacent core member 50 when at least one of the memory elements 20a,b moves to assume its predetermined shape. The sleeve 112 also interconnects one memory element to another memory element so that when one memory element moves in a first direction to assume its preset shape a force is applied to move the other memory element in the first direction and vice versa.

Desirably, the sleeve 112 is a resilient tubular jacket for embracing elastically the core member 50 and the memory elements 20a,b to provide a slip interface therebetween. The sleeve 112 includes an axially inner portion 113 for the reception of a distal end of the core 50 and the tip portions 24 of each memory element and an axially outer portion 114 for the reception of a forward tip portion of the core. Thus, each memory element received within the sleeve 112 simultaneously is retainable in a core-guiding position as shown in FIGS. 9-11 and is movable with the sleeve 112 to deflect the distal end of the core 50 to a selected position (e.g. the deflected position illustrated in FIG. 11).

The sleeve 112 includes an inner wall 115 defining a slip chamber 116 in which each memory element is able to slip in relation to the core member 50 during selective heating of at least one of the memory elements 20. In preferred embodiments, the sleeve 112 is formed of thin MYLAR material having a thickness of about 0.001 inch. Any other similar material that has a low coefficient of friction and is not generally susceptible to deformation under heat would be suitable.

Figure 9:
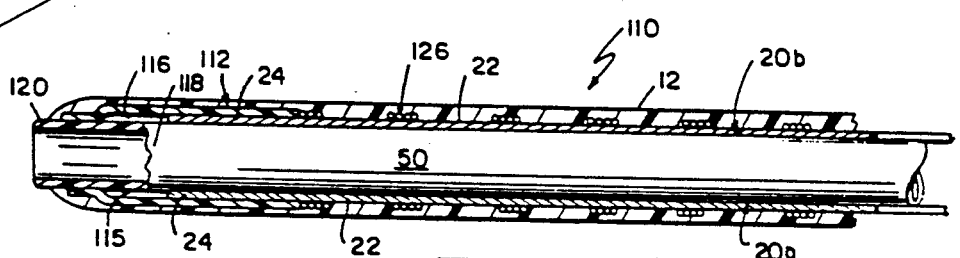
FIG. 9 is a longitudinal sectional view, partly broken away, showing the embodiment of FIG. 8 in its relaxed position and taken generally along section lines 9—9 of FIG. 8.

As shown best in FIGS. 8 and 9, the core 50 includes a distal end 118 having a forward tip portion 120. Installation of the sleeve 112 operates to position the forward tip portion 24 of each memory element 20a,b in close proximity to the distal end 118 of the core 50. The first and second memory elements 20a,b are positioned on opposite sides of the core 50 in spaced relation as shown in FIGS. 8, 9, and 11 so that the core 50 is intermediate the two memory elements. Thus, the forward tip portion 24 of each memory element is retained in its core-guiding position by sleeve 112. In addition, the remaining body portion 22 of each memory element is retained in its core-guiding position by means of a wrap.

Figure 10:
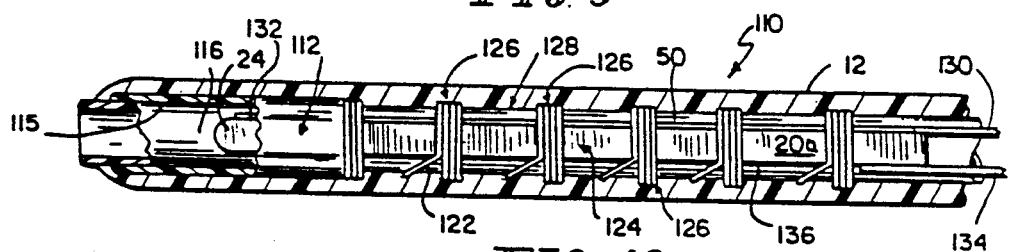
FIG. 10 is a view, partly broken away, of the embodiment of FIG. 9 rotated 90° about its longitudinal axis.
Figure 11:
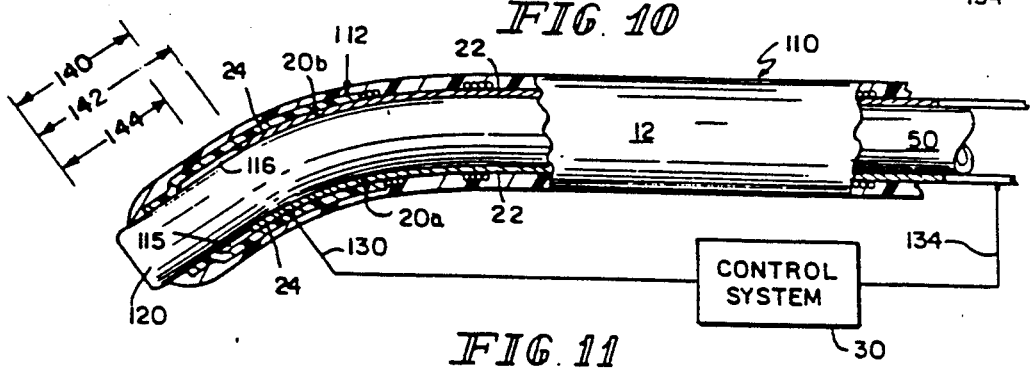
FIG. 11 is a longitudinal sectional view, partly broken away, showing the embodiment of FIG. 8 in a deflected position.

The memory element retaining wrap is desirably a continuous filament 122 as illustrated in FIGS. 8-11. For example, a nylon filament having a 0.002 inch diameter would be satisfactory. The filament wrap 122 couples at least a segment of the body portion 22 of each memory element 20a,b to the core 50 so that the body remaining portion segment is permitted to slip in relation to the adjacent core 50 when at least one of the memory elements 20a,b moves to assume its preset shape. Desirably, the filament wrap 122 embraces a radially outwardly facing surface 124 of each of the memory elements in sufficiently tight relation to retain the memory elements in their coupled position while permitting relative slipping movement between each coupled memory element and the core 50. As shown in FIGS. 8 and 10, the continuous filament 122 defines a plurality of winding bunches 126 disposed along the length of the core 50 in spaced-apart relation so that each winding in a winding bunch 126 can move along the core in relation to one another in the spaces 128 therebetween during deflection or bending of the distal end 16 of the tubular member 12. Illustratively, each spaced winding bunch 126 includes three windings as shown in FIGS. 8 and 10.

In the embodiment illustrated in FIGS. 8-11, the temperature-activated memory elements 20a,b are electrically connected to the control device 34 by wire 130 of rectangular cross-section. The remainder of rectangular wire 130 is mounted along the side edge 132 of the remaining portion 22 of each memory element 20. Return or ground wire 134 is also of rectangular cross-section and mounted along another side edge 136 of each memory element at a proximal end of the remaining body portion 22 of the memory element. Other suitable electrical coupling means are usable to couple the memory elements of the embodiment of FIGS. 8-11 to the control device 34 without departing from the scope of the present invention.

In operation, the sleeve 112 included in the embodiment of FIGS. 8-11 provides numerous advantages. One advantage is that maneuverability of the catheter 110 is improved due to slippage of each memory element 20a,b relative to core 50 in the slip chamber 116 defined by the sleeve 112. A certain amount of slippage is desirable to allow relative movement of the memory elements 20 and the core 50 to improve the flexibility of the catheter. As shown best in FIG. 11, movement of the first memory element 20a to assume its predetermined position causes the forward tip portion 24 of the first memory element 20a to move along the exterior surface of the core 50 toward the forward tip portion 120 of the core 50 and the forward tip portion 24 of the second memory element 20b to move along the exterior surface of the core 50 away from the forward tip portion 120 of the core 50. In other words, the first memory element 20b is arcuately shaped when the memory element 20a moves to assume its predetermined shape and vice versa. In particular, the arc defined by the memory element 20a is smaller than the arc defined by the equidistantly spaced-apart memory element 20b as shown in FIG. 11. The slippage of memory elements 20a and 20b relative to the forward tip portion 120 of core 50 is shown by the arrows in FIG. 11. Arrow 140 represents the positions of the tips 24 before deflection and arrows 142 and 144 represent the positions of the tips 24 of elements 20b and 20a respectively when the catheter is deflected.

Figure 12:
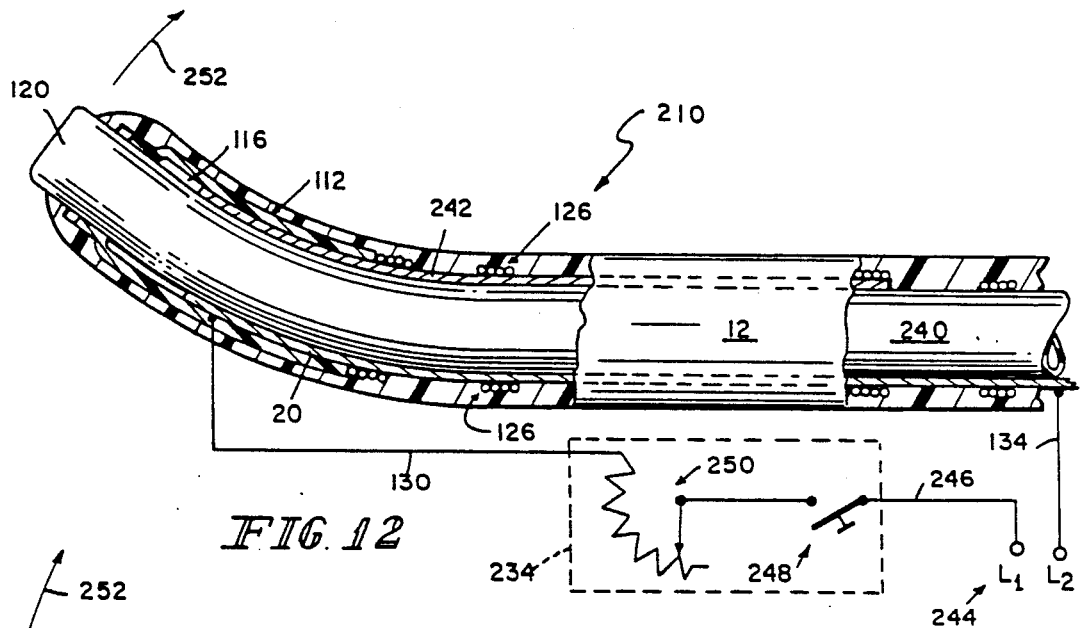
FIG. 12 is a longitudinal sectional view of yet another embodiment of the present invention, partly broken away, showing the distal end of a guide apparatus in a relaxed position.
Figure 13:
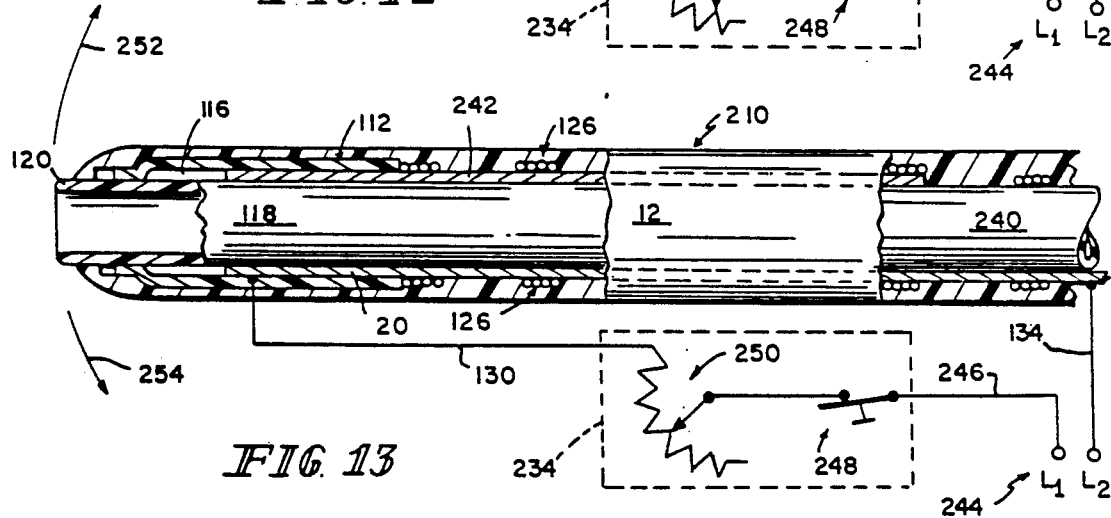
FIG. 13 is a view of the embodiment of FIG. 12, partly broken away, showing the distal end of the guide apparatus in a partially deflected position.
Figure 14:
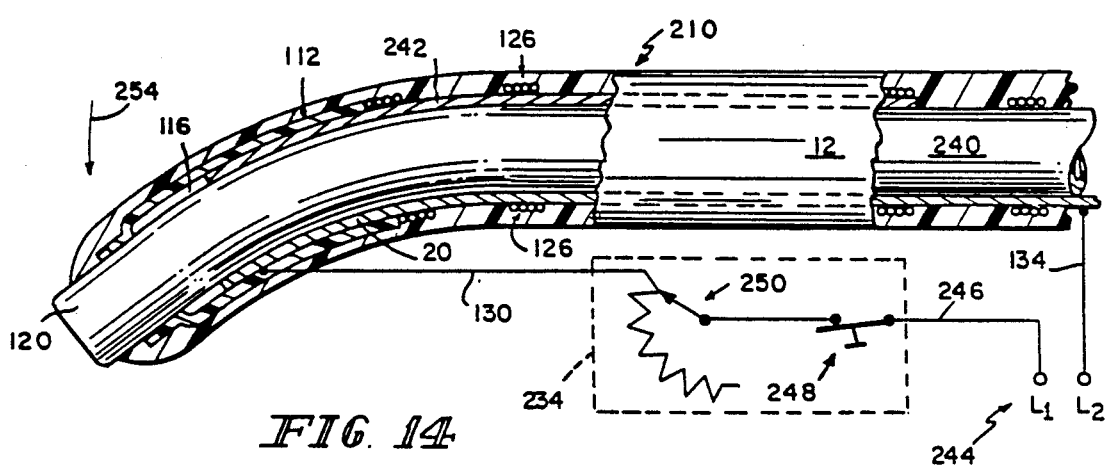
FIG. 14 is a view of the embodiment of FIG. 12, partly broken away, showing the distal end of the guide apparatus in a fully deflected position.

Still another embodiment of the present invention is shown in FIGS. 12-14. Reference numerals from FIGS. 1-4 and 8-11 have been applied to a catheter 210 as shown in FIGS. 12-14 where the same or similar parts are being used. Catheter 210 includes a tubular member 12, a temperature-activated memory element 20, and a sleeve 112 of the types described above.

An electrically insulative hollow core member 240 is provided in the interior of tubular member 12 for receiving medical instruments, fiber optics lines, fluid-conducting tubes, or other medical or optical tools. Core member 240 is desirably made of plastics material such as urethane, TEFLON, KYNAR, or polyethylene and has a wall thickness of 0.005-0.010 inch (1.27-2.54 mm). In contrast to the core members illustrated in connection with the embodiments of FIGS. 1-11 that are generally straight in their relaxed positions, core member 240 is preformed using known techniques to assume a curved shape in its relaxed position as shown in FIG. 12.

The catheter 210 further includes a spring 242 positioned on the exterior of curved core member 240 in diametrically opposed relation to memory element 20. The spring 242 is desirably made of stainless steel or plastics material and has a thickness of 0.010 inch (2.54 mm). The spring 242 is also preformed using known techniques to assume a curved shape. As shown in FIG. 12, the radius of curvature of preformed spring 242 is less than the radius of curvature of curved core member 240.

Spring 242 effectively serves as a resilient memory element and cooperates with core 240 to load memory element 20 with a force that bends memory element 20 to an initial shape illustrated in FIG. 12. The spring constant of spring 242 is selected to cause spring 242 to bend the distal end of the catheter in one direction as shown in FIG. 12 and also yield under loading provided by the heated memory element 20 to permit the distal end of the catheter to bend in an opposite second direction as shown in FIGS. 13 and 14.

Sleeve 112 slidably couples memory element 20 and preformed spring 242 to curved core member 240 so that the memory element 20 and spring 242 are permitted to slip in relation to the adjacent core member 240 when either of the memory element 20 and the spring 242 move to assume its preset shape. The sleeve 112 also interconnects memory element 20 to spring 242 so that when the memory element 20 moves in a first direction 254 to assume its preset shape a force is applied to move the spring 242 in the first direction 254 and vice versa.

In the diagrammatic embodiment illustrated in FIGS. 12-14, the temperature-activated memory element 20 is electrically connected to a control device 234 and a power supply 244 by wires 130, 134, and 246. Control device 234 includes switch means 248 and power control means 250. Switch means 248 is operable to decouple the power supply 244 and the memory element 20 to prevent heating of memory element 20. Power control means 250 is operable to vary the electrical power provided to memory element 20, thereby regulating the amount of heat applied to memory element 20. Illustratively, power control means 250 is a rheostat. It will be appreciated by those skilled in the art that the manner of controlling the temperature of memory element 20 can be accomplished using a variety of control systems other than the illustrated system without departing from the scope of the present invention.

One exemplary operation sequence of catheter 210 is illustrated in FIGS. 12-14. In particular, the relaxed state of the distal end of tubular member 12 is shown in FIG. 12. The preset curved shapes of core member 240 and spring 242 act to bend the distal end of tubular member 12 in direction 252 as shown in FIG. 12. At this stage, switch means 248 is in its open circuit position, preventing current generated by power supply 244 from being applied to heat the memory element 20. Thus, the relatively cool memory element 20 is also bent in direction 252 due to the interconnection with core member 240 and spring 242 established by sleeve 112 and tubular member 12. Such bending resulting from the preset curved shapes of core member 240 and spring 242 effectively defines an "initial position" of the memory element 20 and the distal end tubular member 12.

Steering and aiming of catheter 210 is accomplished by operation of control device 234 in the following manner. Once switch means 248 is moved to its closed circuit position shown in FIGS. 13 and 14, the operator can control the heating and cooling of the temperature-activated memory element 20 by using power control means 250.

Movement of power control means 250 to a first setting illustratively depicted in FIG. 13 causes a sufficient amount of power to be applied to memory element 20 so that the memory element 20 is heated and moves in direction 254 away from its initial curved shape to assume a substantially straight shape. The steering force generated by such movement is transmitted to core member 240 and spring 242 in part via sleeve 112. This steering force is sufficient to overcome opposing "return" forces generated by core member 240 and spring 242.

Continued movement of power control means 250 to another power setting illustratively depicted in FIG. 14 causes still more power to be applied to memory element 20. This heats memory element 20 to a higher "predetermined" temperature, causing the memory element 20 to continue to move in direction 254 to assume a "predetermined" curved shape.

Return of the catheter 210 to its initial relaxed state shown in FIG. 12 is easily accomplished by using control device 234 to lessen the amount of power applied to memory element 20. This step allows memory element 20 to cool, thereby permitting preset core member 240 and spring 242 to cooperate to exert a return force on the distal end of the tubular member 12 and memory element 20. Such a return force acts in direction 252 in the absence of a steering force generated by memory element 20, thereby causing catheter 210 to be returned to its relaxed state.

It will be appreciated that a plurality of pairs of temperature-activated memory elements 20 and springs 242 could be positioned in the distal end of the catheter to provide a great deal of flexibility in steering and aiming the catheter. However, it will be understood that it is possible to steer and aim a catheter provided with only a single temperature-activated memory element 20 and return spring 242 in a multiplicity of radial directions by rotating the catheter about its central longitudinal axis during heating of memory element 20 using control device 234.

Several other embodiments of the present invention are shown in FIGS. 15-21. In each of the embodiments illustrated in FIGS. 15-21, a heatable temperature-activated memory element is positioned within a guide wire made of spring material. In the embodiment illustrated in FIG. 19, the guide wire is made out of a resilient shape-memory alloy so that the guide wire itself performs both a memory function and a spring return function.

FIGS. 15-21 illustrate preferred embodiments of using a temperature-activated shape-memory alloy to deflect a guide wire or the like. Although such steerable guide wire assemblies are easily installed in catheters as shown, it will be appreciated that the steerable guide wire concept has much broader application and does not necessarily have to be inserted within a catheter. In other words, the guide wire itself can provide a catheter for insertion into canals, vessels, passageways, or body cavities to permit injection or withdrawal of fluids or to keep a passage open.

Figure 15:
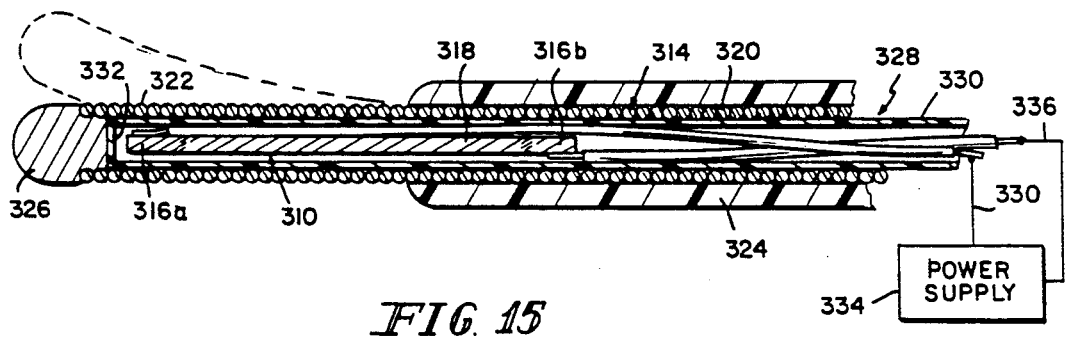
FIG. 15 is a longitudinal sectional view of another embodiment of the present invention showing a temperature-activated memory element positioned within a coiled spring.

One embodiment of a steerable guide wire assembly is illustrated in FIG. 15. Memory element 310 is positioned in an interior chamber 312 of guide wire 314. Memory element 310 is oriented to deflect guide wire 314 from an initial position (solid lines) to a deflected position (phantom lines) upon bending movement of memory element 310 to assume a predetermined bent shape (not shown).

Memory element 310 is desirably made of a shape-memory alloy such as nitinol and configured to include a pair of lead-attachment portions 316a, b and a shape-memory portion 318. Reference is hereby made to U.S. Pat. No. 4,777,799, entitled "Memory Element" and filed concurrently herewith, for a description of the construction, function, and operation of portions 316 and 318.

Guide wire 314 is desirably a coil made of TEFLON-coated 304 stainless steel spring material. Guide wire 314 includes a proximal portion 320 disposed in base 324 and a distal portion 322 to provide an assembly for steering and aiming the base 324. It will be understood that base 324 can be configured to provide a catheter, cannula, or the like for receiving guide wire 314 or that guide wire 314 can function in accordance with the present invention on its own as a catheter independent of any such base means.

A rounded cap 326 is coupled to the distal portion 322 of guide wire 314 to provide a smooth probe tip for the assembly. An insulative sleeve 328 having a side wall 330 and a top wall 332 is positioned in the interior chamber 312 of guide wire 314 so that top wall 332 lies in abutting relation to cap 326 and side wall 330 lies intermediate guide wire 314 and memory element 310. Advantageously, insulative sleeve 328 prevents electrical communication between memory element 310 and each of guide wire 314 and cap 326.

An electrical system is provided for selectively heating memory element 310 to a temperature in excess of its transition temperature by varying the current passing through memory element 310 so that memory element 310 moves to assume a predetermined shape and deflect guide wire 314. Such deflection results from engagement of guide wire 314 by the moving memory element 310 disposed within interior chamber 312 of guide wire 314. Thus, movement of guide wire 314 is induced by moving memory element 310 without depending upon a fixed coupling between guide wire 314 and memory element 310. The electrical system includes a power supply 334, first lead means 336 for electrically connecting one terminal of the power supply 334 to lead-attachment portion 316b, and second lead means 338 for electrically connecting another terminal of power supply 334 to lead-attachment portion 316a.

Figure 16:
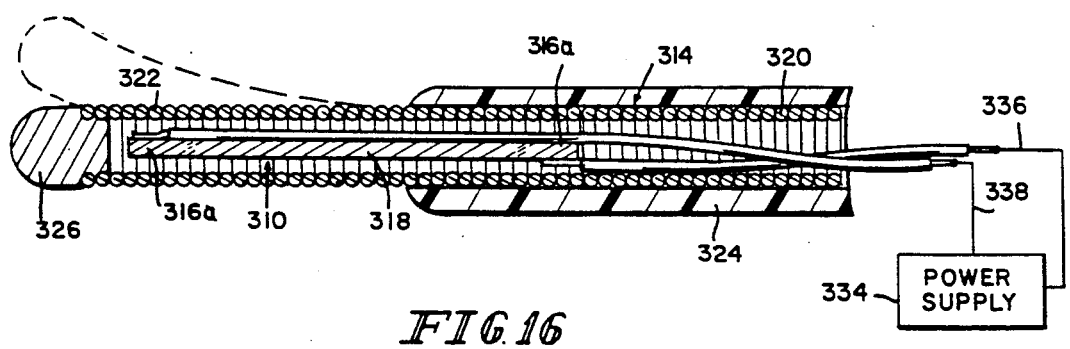
FIG. 16 is a longitudinal sectional view of yet another embodiment of the present invention.

Another embodiment of the invention is illustrated in FIG. 16. Reference numerals from FIG. 15 have been applied to the assembly as shown in FIG. 16 where the same or similar parts are being used. In this embodiment, an insulative coating material (not shown) is applied to at least one of memory element 310, guide wire 314, and cap 326 in lieu of insulative sleeve 328. Thus, the insulative coating also acts to prevent change in the magnitude of current flowing through memory element 310 due to either incidental or sustained contact with guide wire 314 and/or cap 326 during movement of memory element 310 upon being heated above its transition temperature.

Figure 17:
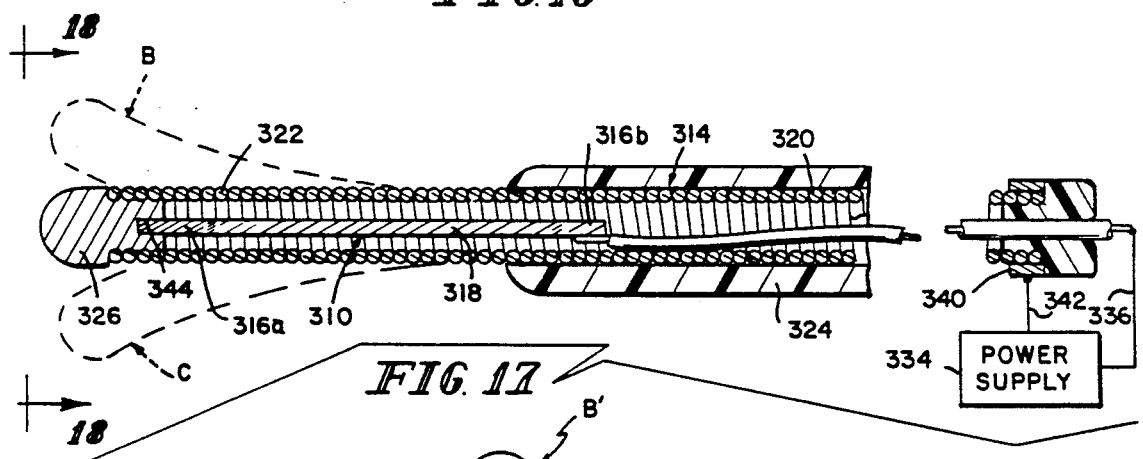
FIG. 17 is a longitudinal sectional view of still another embodiment of the present invention showing a type of circuit means different than that shown in FIGS. 15 and 16.

Yet another embodiment of the invention is illustrated in FIG. 17. Reference numerals from FIGS. 15 and 16 have been applied to the assembly as shown in FIG. 17 where the same or similar parts are being used. In this embodiment, the second lead means is different than that shown in FIGS. 15 and 16 in that the power supply 334 and lead-attachment portion 316a are electrically coupled by means of an electrical connection established by cap 326, guide wire 314, band 340, and lead 342.

Cap 326 includes slot 344 for receiving lead-attachment portion 316a and is made of an electrically conductive material. Preferably, lead-attachment portion 316a is welded or soldered in place in slot 344. Alternatively, a mechanical connection could be employed by deforming cap 326 about memory element 310 to clamp lead-attachment portion 316a in place. Conductive band 340 electrically communicates with proximal portion 320 of guide wire 314 and lead 342 to introduce current from power supply 334 to conductive guide wire 314 for distribution to lead-attachment portion 316a of memory element 310. It will be appreciated that either an insulative sleeve or coating of the types described above could be employed to prevent unwanted electrical communication between memory element 310 and guide wire 314.

Figure 18:
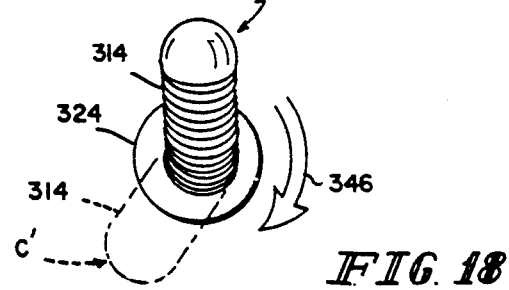
FIG. 18 is a transverse sectional view, taken generally along lines 18—18 of FIG. 17, showing rotation of a guide wire in a clockwise direction about its longitudinal axis in response to heating the temperature-activated memory element inside above its transition temperature.

FIG. 18 illustrates rotation of guide wire 314 about its longitudinal axis in in response to heating memory element 310 above its transition temperature so that memory element 310 moves to assume its predetermined shape. The solid line position B' of guide wire 314 in FIG. 18 corresponds to the bent phantom line position B in FIG. 17, while phantom line C' in FIG. 18 corresponds to solid line position C in FIG. 17. Thus, in FIG. 18, the guide wire is not shown in its straight position, but rather in each of two of its bent positions. Double arrow 346 represents rotational movement of guide wire 314 relative to base 324.

It has been observed that the above-described rotational movement occurs during use of each of the embodiments illustrated in FIGS. 15-17 and 19-21. In particular, cap 326 moves along a path (not shown) orbiting its initial position shown in solid lines in FIGS. 15-17 and 19-21 during deflection of the guide wire 314 by the heated memory element 310. The guide wire 314 is coiled or otherwise configured to provide means for converting bending forces applied to the guide wire 314 by the memory element 310 to rotation-inducing forces so that the guide wire 314 rotates about its longitudinal axis in response to movement of memory element 310 to assume its predetermined bent shape. It has further been observed that the amount of rotation is controlled by the amount of current applied.

In each of the embodiments of FIGS. 15-17, 20, and 21, the guide wire 314 is configured to apply a yieldable biasing force to the memory element 310 upon engagement of guide wire 314 and memory element 310 so that memory element 310 is moved to assume a shape (e.g., straight) other than its predetermined bent shape upon cooling of the memory element 310 to a temperature below its transition temperature. Advantageously, guide wire 314 provides yieldable means for returning a cooling memory element to its initial straight position after being heated to assume a predetermined bent position. Such a "yieldable" construction advantageously does not interfere with movement of the memory element 310 to assume its predetermined position.

Figure 19:
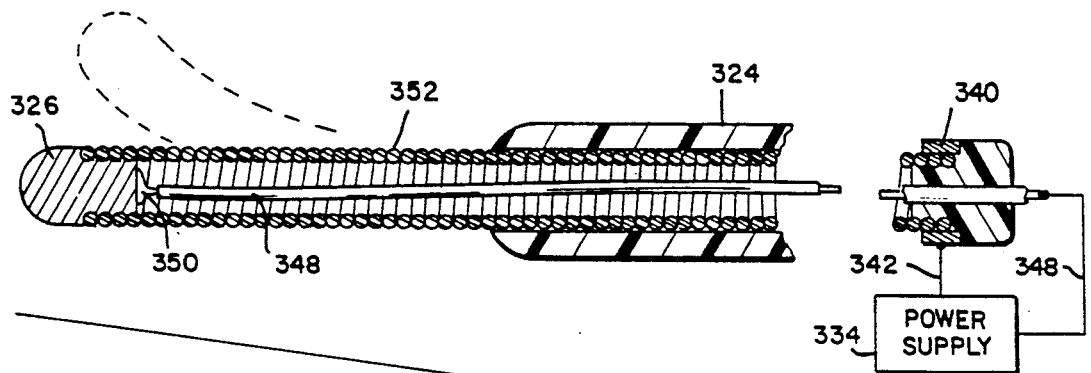
FIG. 19 is a longitudinal sectional view of yet another embodiment of the present invention having a temperature-activated memory element configured to provide its own spring return means.

Still another embodiment of the invention is illustrated in FIG. 19. Reference numerals from FIGS. 15-18 have been applied to the assembly as shown in FIG. 19 where the same or similar parts are being used. In this embodiment, guide wire 352 is made of an electrically conductive shape-memory alloy and is configured to provide both the "spring return function" of guide wire 314 and the "deflection inducing function" of memory element 310.

Power supply 334 is electrically coupled to cap 326 by lead 348 at junction 350. Thus, power supply 334 can be used to vary the current through the temperature-activated guide wire 352 to alter the shape of the guide wire 352. The spring construction of guide wire 352 will cause it to resume its initial position upon cooling to a temperature below its transition temperature on its own volition. Advantageously, such a construction reduces manufacturing costs and problems.

Figure 20:
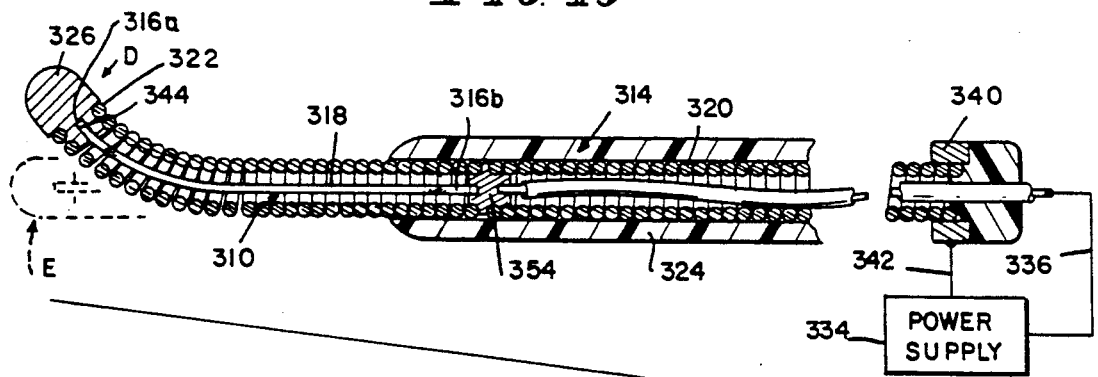
FIG. 20 is a longitudinal sectional view of still another embodiment of the present invention having a double-anchored temperature-activated memory element arranged to apply pulling force to its companion spring return means during movement of the memory element to assume a predetermined shape under thermal loading.

Yet another embodiment of the invention is illustrated in FIG. 20. Reference numerals from FIGS. 15-18 have been applied to the assembly as shown in FIG. 20 where the same or similar parts are being used. In this embodiment, memory element 310 is mounted to apply pulling forces to cap 326, thereby inducing movement of guide wire 314 to assume a different position.

One characteristic thermal property of shape-memory alloys generally is that such alloys exhibit a negative coefficient of thermal expansion. In other words, shape-memory alloys contract when heated and expand, at least under an externally applied load, when cooled. It will be appreciated that the change in length per unit of length per degree change of temperature is practically constant for each shape-memory alloy. Thus, one can select or design a particular shape-memory alloy which will contract in a predetermined manner upon heating of the alloy to its transition temperature.

The embodiment illustrated in FIG. 20 is configured to exploit the above-noted thermal expansion property of shape-memory alloys by anchoring the memory element 310 at its opposite ends 316a, b so that memory element 310 will apply an axial compression load to cap 326 as it contracts under heat. Such loading will tend to pull cap 326 and the attached distal portion 322 of coiled spring 314 from the bent solid line position D to FIG. 20 to the straight phantom line position E also in FIG. 20.

In the embodiment of FIG. 20, memory element 310 is annealed to have a straight predetermined shape so that if memory element 310 is bent or twisted while cool and then heated to its transition temperature, it will move to regain its original straight shape. Also, guide wire 314 is preformed to have a bent shape at its distal end, one example of which is illustrated in FIG. 20. Thus, guide wire 314 will act to deflect the memory element 310 housed within as long as the memory element 310 is cooled below its transition temperature.

Plug means 354 is disposed in the interior chamber 312 of guide wire 314 and rigidly fixed to proximal portion 320 as illustrated in FIG. 20. It is within the scope of the present invention to insert and mount the plug 354 in guide wire 314 using a variety of techniques, including, for example, providing a plug having external threads for threadedly engaging a coiled spring. Of course, adhesive, soldering, welding, or the like can be employed to provide suitable alternatives.

Plug means 354 desirably has at least an electrically conductive portion for interconnecting lead-attachment portion 316b of memory element 310 to first lead means 336 to establish an electrical path coupling memory element 310 and power supply 334. It will be appreciated that insulation means can be interposed between the electrically conductive portion of plug means 354 and guide wire 314 to prevent electrically conductive contact therebetween. Insulation means, for example, could comprise a separate element, a coating, or a portion of plug means 354.

In the illustrated embodiment, first anchor means is provided, in part, by a coupling of the distal lead-attachment portion 316a to the end cap 326 while a second anchor means is provided, in part, by a coupling of the proximal lead-attachment portion 316b to fixed plug means 354. Although memory element 310 is effectively anchored at its opposite ends to spaced-apart portions of guide wire 314, significant temperature stresses will not develop in the memory element 310 since the memory element 310 enjoys sufficient freedom for expansion and contraction due to the lengthening and shortening of resilient guide wire 314.

In operation, the bent memory element 310 shown in solid lines in FIG. 20 will both straighten and contract to the phantom line position in FIG. 20 upon being heated to its transition temperature. One result of such straightening is that a transverse shear load will be applied to cap 326 by the memory element 310, which load will tend to urge guide wire 314 toward its straightened phantom line position. One result of such contraction is that an axial compression load will be applied to cap 326 by the double-anchored memory element 310, which load will tend to pull the distal portion 32 of the guide wire 314 toward the proximal portion 320 to assist substantially in moving the guide wire to its straightened phantom line position. Thus, these transverse shear load and axial compression load cooperate to induce movement of the guide wire to its straightened phantom line position.

One advantage of this feature is that contraction of a shape-memory alloy under heat is used to apply additional movement-inducing forces to the distal portion 322 of guide wire 314. By generating such new forces, it is possible to decrease the size and mass of memory element 310 without significantly degrading the force generation potential of such a memory element. It will be understood that it is within the scope of the present invention to exploit expansion/contraction of the widths or other dimensions of memory elements 310 to generate such guide wire-pulling forces of the type described above and that the invention is not just limited to length expansion/contraction as illustrated in a preferred embodiment as shown in FIG. 20.

Figure 21:
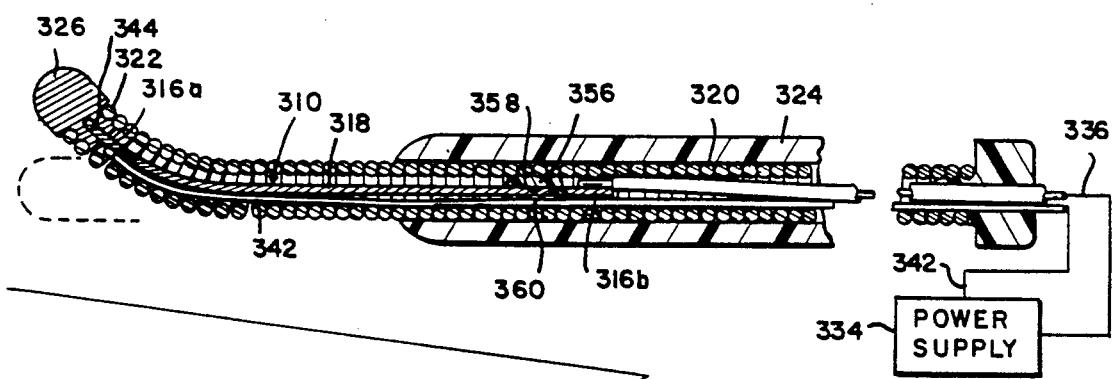
FIG. 21 is a longitudinal sectional view of yet another embodiment of the present invention having a double-anchored temperature-activated memory element coupled directly to a current source.

Still another embodiment of the invention is illustrated in FIG. 21. Reference numerals from FIGS. 15–18 and 20 have been applied to the assembly as shown in FIG. 21 where the same or similar parts are being used. In this embodiment, a double-anchored memory element of the type shown in FIG. 20 is directly coupled to power supply 334.

Plug means 356 is configured to accommodate a different technique for mounting memory element 310 and applying a current to memory element 310. Nevertheless, plug means 356 is assembled and functions in a manner similar to plug means 354. As shown in FIG. 21, plug means 356 is formed to include first passageway means 358 for allowing memory element 310 to extend through plug means 356 and second passageway means 360 for allowing lead 352 to extend through plug means 356.

Memory element 310 is anchored to plug means 356 using any suitable external and/or internal coupling means (e.g., epoxy, adhesive, weld, solder, clamp, etc.). It will be appreciated that in the case of welding, soldering, or the like the lead attachment portion 316b will be sized and positioned relative to plug means 356 to accommodate any such welding or the like to the plug means 356 to preserve the shape-memory characteristics of shape-memory portion 318. Lead 336 is electrically coupled to the rearwardly extending exposed end of lead-attachment portion 316b. Lead 342 extends into interior chamber 312 and through second passageway means 360 and is electrically coupled to lead attachment portion 316a adjacent to the point at which lead attachment portion 316a is anchored to cap 326. In this embodiment, current from power supply 334 is passed directly to memory element 310 via leads 336, 242 without passing through guide wire 314.

While illustrative embodiments and uses of guide apparatus, probes, and the like embodying the present invention have been shown and described, it will be appreciated that various modifications may be made to the illustrative embodiments without departing from the scope of the present invention.

What is claimed is:

1. A variable shape guide apparatus comprising
   a temperature-activated memory element moving in a first direction to assume a predetermined shape when heated to a predetermined temperature,
   spring means housing the memory element for yieldably urging the memory element in a second direction away from the first direction upon cooling of the memory element to a temperature less than the predetermined temperature so that the memory element is moved to assume a shape other than the predetermined shape, the spring means having an original shape alterable by movement of the memory element in its first direction toward its predetermined shape,
   insulation means for preventing electrically conductive contact between the memory element and the spring means, and
   control means for selectively heating the memory element so that the memory element is moved in the first direction against the urging of the spring means to permit an operator to alter the shape of the spring means automatically by heating the memory element, whereby the spring means is allowed to resume its original shape upon cooling of the memory element housed in the spring means.

2. The apparatus of claim 1, wherein the insulation means is provided by an insulative member situated intermediate the memory element and the spring means.

3. The apparatus of claim 1, wherein the insulation means is provided by a coating material on at least one of the memory element and the spring means.

4. A variable shape guide apparatus comprising a flexible guide member having an original shape and being formed to include an interior cavity, a temperature-activated memory element within the interior cavity of the flexible guide member, the memory element moving against the flexible guide member to assume a predetermined shape when heated to a predetermined temperature, thereby altering the shape of the flexible guide member, the guide member providing spring means for yieldably applying a biasing force to the memory element so that the memory element is moved to assume a shape other than the predetermined shape upon cooling of the memory element to a temperature less than the predetermined temperature, thereby allowing the flexible guide member to resume its original shape, and control means for selectively heating the memory element so that the memory element is moved to assume its predetermined shape and alter the shape of the flexible guide member, whereby the guide member is allowed to resume its original shape upon cooling of the memory element.

5. The apparatus of claim 4, further comprising insulation means for preventing electrical communication between the memory element and the guide member.

6. The apparatus of claim 5, wherein the insulation means includes at least one of a sleeve positioned in the cavity intermediate the memory element and the guide member and a coating material on at least one of the memory element and the guide member.

* * * * *